(12) United States Patent
Grass et al.

(10) Patent No.: US 11,539,516 B2
(45) Date of Patent: Dec. 27, 2022

(54) ENCODING AND DECODING INFORMATION IN SYNTHETIC DNA WITH CRYPTOGRAPHIC KEYS GENERATED BASED ON POLYMORPHIC FEATURES OF NUCLEIC ACIDS

(71) Applicant: ETH ZURICH, Zürich (CH)

(72) Inventors: Robert N. Grass, Zürich (CH); Wendelin Jan Stark, Langenthal (CH)

(73) Assignee: ETH ZURICH, Zürich (CH)

( * ) Notice: Subject to any disclaimer, the term of this patent is extended or adjusted under 35 U.S.C. 154(b) by 235 days.

(21) Appl. No.: 16/757,847

(22) PCT Filed: Sep. 25, 2018

(86) PCT No.: PCT/EP2018/075981
§ 371 (c)(1),
(2) Date: Apr. 21, 2020

(87) PCT Pub. No.: WO2019/081145
PCT Pub. Date: May 2, 2019

(65) Prior Publication Data
US 2021/0194686 A1    Jun. 24, 2021

(30) Foreign Application Priority Data
Oct. 27, 2017  (CH) .................................... 01304/17

(51) Int. Cl.
*H04L 29/06*     (2006.01)
*G06F 21/00*     (2013.01)
(Continued)

(52) U.S. Cl.
CPC ............ *H04L 9/0866* (2013.01); *G16B 20/20* (2019.02); *G16B 30/00* (2019.02); *H04L 9/0618* (2013.01); *H04L 9/30* (2013.01); *H04L 2209/34* (2013.01)

(58) Field of Classification Search
CPC ........ H04L 9/0866; H04L 9/0618; H04L 9/30; H04L 2209/34; G16B 20/20; G16B 30/00; G16B 20/00; G16B 25/00
See application file for complete search history.

(56) References Cited

U.S. PATENT DOCUMENTS 9,384,320 B2 *   7/2016   Church .................. G06N 3/123
2013/0019103 A1 *   1/2013   Read ..................... H04L 9/3228
                                                      713/183

(Continued)

FOREIGN PATENT DOCUMENTS

WO          2013178801         12/2013

OTHER PUBLICATIONS

International Search Report and Written Opinion for corresponding International Application No. PCT/EP2018/075981 dated Mar. 1, 2019.

*Primary Examiner* — Lisa C Lewis
(74) *Attorney, Agent, or Firm* — Renner, Otto, Boiselle & Sklar, LLP

(57) ABSTRACT

The invention is notably directed to a method for encoding information. This method first comprises generating an encryption key according to polymorphic features of nucleic acids from one or more entities. Next, information is encrypted based on the generated key. Finally, the encrypted information is encoded into synthetic DNA. Another aspect concerns a method for retrieving information. Consistently with the above encoding scheme, synthetic DNA in provided, which encodes encrypted information. Such information is read by sequencing the synthetic DNA and by decrypting the information read using a decryption key. The latter is generated according to polymorphic features of nucleic acids from one or more entities (e.g., from the legitimate individual(s) requesting access to information). Thus, the encoded information cannot be interpreted unless (Continued)

a suitable decryption key is available. The invention is further directed to related DNA samples and systems, including DNA vaults.

20 Claims, 4 Drawing Sheets

(51) Int. Cl.
*H04L 9/08* (2006.01)
*G16B 20/20* (2019.01)
*G16B 30/00* (2019.01)
*H04L 9/06* (2006.01)
*H04L 9/30* (2006.01)

(56) References Cited

U.S. PATENT DOCUMENTS

| | | | | |
|---|---|---|---|---|
| 2015/0254912 | A1* | 9/2015 | Weisman | H04L 9/0866 |
| | | | | 705/325 |
| 2015/0319152 | A1* | 11/2015 | Chastain | H04L 63/062 |
| | | | | 726/4 |
| 2016/0072800 | A1* | 3/2016 | Soon-Shiong | H04L 63/0861 |
| | | | | 726/7 |
| 2017/0272245 | A1* | 9/2017 | Norton | H04L 9/0863 |

* cited by examiner

ENCODING AND DECODING INFORMATION IN SYNTHETIC DNA WITH CRYPTOGRAPHIC KEYS GENERATED BASED ON POLYMORPHIC FEATURES OF NUCLEIC ACIDS

This application is a national phase of International Application No. PCT/EP2018/075981 filed Sep. 25, 2018 and published in the English language, which claims priority to Swiss Application No. 01304/17 filed Oct. 27, 2017, both of which are incorporated herein by reference.

BACKGROUND

The invention relates in general to methods for encoding or retrieving information stored on synthetic DNA, as well as related systems (sequencing devices and apparatus) and synthetic materials. In particular, the invention is directed to techniques for making data encoded in synthetic DNA useful (i.e., interpretable) only to one or more predefined individuals.

Techniques to encode information in synthetic DNA are known, wherein digital information is translated (using a given translation method) into a sequence combining the four natural nucleotides (adenine, cytosine, guanine and thymine). The sequence is then synthesized into physical DNA. In this form the data can be stored in a highly compact way (with high storage density) and for long storage durations (see, e.g., U.S. Pat. No. 9,384,320 and WO2013178801 and references therein). For information retrieval the DNA is sequenced, and digital information can be recovered using the inverse of the translation method. The unique advantages of using DNA as a data carrier are its extremely high data density (>200 exabytes per gram) and the high stability of the data-encoding medium. Both features are of especial importance if sensitive information is to be stored. I.e., the compact (small size) storage medium is useful to conceal the encoded material, while its stability in time results in that data does not have to be regularly copied (duplicated) to maintain data integrity.

A downside of such techniques is that anyone who has access to the information-encoding medium (the synthetic DNA) and the translation method may be able to recover the information.

Besides, at a time of all-pervasive Internet and social media, the secure storage of digital data (including, e.g., personal data, proprietary data and confidential data, etc.) is a challenge. Commonly used access control methodologies employ passwords (websites) and key generators (e.g., as in online banking). In addition, biometrics authentication is often used for identification and access control purposes. Examples include fingerprint scanners (as in cell phones), iris scanners (room access), face recognition (surveillance), signature (official documents).

Such methods provide various strengths of authentication. While they can easily be implemented in a computerized context (e.g., where the device used to authenticate the requester is otherwise used to access the data), the above methods are not perceived as being suitable for the former context, where information is encoded as synthetic DNA. Thus, a novel approach is needed to secure access rights to information encoded in synthetic DNA.

SUMMARY

According to a first aspect, the present invention is embodied as a method for encoding information. This method first comprises generating an encryption key according to polymorphic features of nucleic acids from one or more entities. Next, information is encrypted based on the generated key. Finally, the encrypted information is encoded into synthetic DNA (e.g., including one or more samples of synthetic DNA). A complementary aspect relates to a corresponding method for retrieving information, wherein information read is decrypted using a decryption key, which need be generated according to polymorphic features of nucleic acids from the same entities, e.g., legitimate individual(s) who request access to such information.

Information as considered herein (prior to or after encrypting it) comprises digital data, which is typically encoded as binary data (0 and 1's), although any alphabet may a priori be used as a basis for encrypting information. For example, such information may be encoded as a n-ary code (with n larger than or equal to two).

The encrypted information cannot be interpreted unless a suitable decryption key is available, which requires having access to specific nucleic acids (e.g., solely known to a legitimate requester). As a result, the present scheme ensures a strong authentication, inasmuch as this authentication is reliable enough even when used alone. In addition, both the encryption and decryption schemes may rely on a same (or related) technology as used to encode and decode information, as illustrated in embodiments discussed below. Thus, the authentication mechanism can be implemented on the same device or apparatus as used to encode or decode information, with little or no added complexity, while ensuring appropriate access rights. I.e., only the person(s) who can provide the required nucleic acids can access the information.

As discussed below in detail, the decryption key may for instance be the same as the encryption key used (in a symmetric encryption scheme) or be a private key generated from said polymorphic features (in an asymmetric encryption algorithm), to which a suitable public key is then paired to enable encryption.

Interestingly, additional security can be added by deleting key material after encryption. For example, in a symmetric encryption scheme, the encryption key can be safely deleted after encryption (just like the material used to generate this key), since the required key can later be re-generated, when needed. In an asymmetric encryption scheme, the public key is useless after encryption because decryption requires the corresponding private key. Thus, the private key as first generated to obtain a corresponding public key can be safely deleted after encryption. The private key may later be re-generated, if necessary.

Note, in the present context, nucleic acids are biomolecules that are typically collected from a human subject, in operation. However, such molecules could equivalently be collected from any lifeform or any entity comprising such nucleic acids. Thus, any such entity (animal, plant, cells, bacteria, viruses, etc.) could serve as a basis for the present encryption/decryption methods. The encryption key generation shall typically include steps to measure said polymorphic features of said nucleic acids and translate the measured polymorphic features into a cryptographic key.

In embodiments, the encryption key is generated from the polymorphic features of DNA or RNA of the one or more entities. The encryption key may for example be generated from short tandem repeats of the DNA of the one or more entities. In particular, the encryption key may possibly be generated from alleles identified by sequencing five or more of predefined, genomic loci (e.g., single nucleotide polymorphisms (SNPs), and/or short tandem repeats (STRs)) of the one or more entities.

In embodiments, the encryption key is generated from a set of single nucleotide polymorphisms of the DNA or RNA of the one or more entities. Said set may for instance comprise at least five single nucleotide polymorphisms, which may be identified (during the encryption key generation) by sequencing the nucleic acids of said one or more entities.

In embodiments, the encryption key is generated from polymorphic features of mitochondrial DNA, or from of a Y-chromosome of the one or more entities.

In preferred embodiments, the method further comprises generating one or more helper datasets from the encryption key generated and said polymorphic features. In that case, encoding the encrypted information further comprises storing the one or more helper datasets generated on said synthetic DNA, along with said encrypted information.

As evoked above, said information may notably be encrypted based on a symmetric encryption algorithm, such that said encrypted information can be decrypted using a key identical to said encryption key. I.e., the encryption method may for example involve a method based on the so-called Data Encryption Standard (DES) or the Advanced Encryption Standard (AES). Note, the polymorphic features used in the generation of the key shall preferably have an entropy of at least 64 bits (e.g., of 128 or 256 bits, or more).

Preferably then, the method further comprises, after having encrypted said information, deleting both the encryption key and any material from which said encryption key was generated, without transmitting (or having transmitted) any of the encryption key and said material. This way, no one (i.e., no third party) can have (or has had) access to the encryption key or the material necessary for generating this key (other than for the purpose of implementing the present encryption methods), it being noted that the encryption key can anyway be regenerated by a legitimate individual.

In other embodiments, the method relies on an asymmetric encryption algorithm. Namely, the method further comprises (prior to generating said encryption key): generating a private key based on said polymorphic features of said nucleic acids of a given sample from said one or more entities. That is, the encryption key is generated based on the private key generated and thereby paired to the latter. Information is encrypted based on an asymmetric algorithm, which uses the generated encryption key as a public key, such that said encrypted information can only be decrypted using a key identical to the private key generated in the first place.

In that respect, we note that the present encryption methods may be carried out in different sites. For example, when using an asymmetric encryption, key pairs can be generated on one site, whereas information is encrypted using the encryption (public key) passed to the encryption system, on another site.

In addition, the private key can be generated a first time to generate the corresponding public key, then deleted (after having encrypted the desired information), and subsequently re-generated for decryption purposes, if necessary. In particular, the method may further comprise (after having encrypted said information) deleting both the private key generated and the material from which said private key was generated, without transmitting (or having transmitted) any of the private key and such material (to any third party). Later, a private key can be re-generated based on same polymorphic features of same nucleic acids of another sample from the same entity(ies), so as to be able to decrypt said encrypted information.

Next, as said, another aspect of the invention concerns a method of retrieving information. Consistently with the above encryption scheme, this method relies on synthetic DNA, which encodes encrypted information. The encrypted information is read by sequencing the synthetic DNA and by decrypting the information read using a decryption key. The latter is generated according to polymorphic features of nucleic acids from one or more entities, e.g., from the legitimate individual(s) who request access to the encoded information. And again, such information cannot be interpreted unless a suitable decryption key is available.

In embodiments, reading the encrypted information further comprises sequencing said polymorphic features, so as to generate said decryption key, in order to decrypt the information read.

Reading the encrypted information preferably comprises mixing sequences of the synthetic DNA provided with genomic sequences containing said polymorphic features, whereby sequences of said polymorphic features and sequences of said synthetic DNA are simultaneously sequenced.

The synthetic DNA provided is preferably sequenced based on a massively parallel DNA sequencing method.

In preferred embodiments, the decryption key is generated based on helper data, in addition to said polymorphic features, whereby the latter are combined with said helper data to compute the decryption key (and thereby generate this key).

Such helper data may be conveyed through any convenient channel. Preferably though, helper data is obtained by reading one or more helper datasets stored on said synthetic DNA, along with said encrypted information. Not only this improves security but, in addition, as helper data is safely stored on the synthetic DNA, it can safely be deleted after encryption in that case, which eases the corresponding data management.

In embodiments, the method further comprises (after mixing said sequences): processing a mixture obtained by mixing the sequences of the synthetic DNA with sequences of said nucleic acids to generate a sequencing pool. This pool may then be sequenced using a massively parallel DNA sequencing method, for example. All subsequent computations will thus be based on the data accordingly sequenced.

The present methods of encoding information make it possible to obtain a sample of synthetic DNA encoding information, whereon information is stored in an encrypted form. Consistently with principles underlying the present methods of encoding information, this encrypted form has been obtained thanks to an encryption key generated according to polymorphic features of nucleic acids from one or more entities. I.e., information stored on the synthetic DNA sample(s) is encrypted and therefore useless, unless polymorphic features of nucleic acids from one or more entities (e.g., human subjects) are used to decrypt such information, if necessary in combination with helper data. That is, one or more helper datasets may possibly be stored on said synthetic DNA, along with said encrypted information.

According to a further aspect, the invention may be embodied as a DNA vault, the latter comprising one or more containers storing one or (more likely) several DNA samples such as described above. This vault may notably be a family vault, whereby at least one of the DNA samples stored thereon encodes information encrypted with an encryption key generated according to inherited polymorphic features, as discussed in the detailed description.

Note, the present methods may notably be implemented using a physical system (e.g., a device, an apparatus, or a facility) designed for encoding and/or decoding information. For example, a decoding system may include a collection of DNA samples such as evoked above and may further be configured to receive a decryption sample (including given nucleic acids) and analyze such a sample, whereby polymorphic features of given nucleic acids can be interpreted as a decryption key, in operation. Consistently with present decryption methods, such a system is otherwise configured to read encrypted information as stored on a DNA sample by sequencing the synthetic DNA and by decrypting the information read using a decryption key generated from said decryption sample, in operation.

The above embodiments have been succinctly described and may accommodate a number of variants. Several combinations of the above features may be contemplated. Examples are given in the next section, wherein methods, DNA samples and DNA vaults embodying the present invention are described, by way of non-limiting examples, and in reference to the accompanying drawings.

BRIEF DESCRIPTION OF SEVERAL VIEWS OF THE DRAWINGS

The accompanying figures, where like reference numerals refer to identical or functionally similar elements throughout the separate views, and which together with the detailed description below are incorporated in and form part of the present specification, serve to further illustrate various embodiments and to explain various principles and advantages all in accordance with the present disclosure.

FIG. 1 illustrates a method of encoding information based on an encryption key generated according to polymorphic features of nucleic acids, wherein information is encrypted thanks to the generated key and then encoded into synthetic DNA, as in embodiments;

FIG. 2 depicts a method of retrieving information encoded thanks to a method as in FIG. 1. The information retrieval process uses synthetic DNA encoding encrypted information, which is decrypted using a decryption key. The latter is generated according to polymorphic features of nucleic acids of an entity. The encrypted information is read by sequencing the synthetic DNA provided and decrypting information read using the decryption key. In this example, sequences of the synthetic DNA are mixed with sequences of said polymorphic features, so as to be simultaneously sequenced, as in preferred embodiments;

FIG. 3 illustrates a method to enroll a new individual (using helper data) and allow original information to be accessed by the newly enrolled individual, as involved in embodiments. FIG. 3 notably illustrates a successful data recovery, where the correct key (obtained from nucleic acids of an authorized individual) is used to decrypt information encoded in a sample containing synthetic DNA, as in embodiments;

FIG. 4 illustrates an attempted (failed) data recovery process, where a wrong key (e.g., obtained from nucleic acids of a non-authorized individual) is used to attempt to decrypt information encoded in a sample containing synthetic DNA, as may occur in embodiments.

Similar or functionally similar elements in the figures have been allocated the same numeral references, unless otherwise indicated.

DETAILED DESCRIPTION OF EMBODIMENTS OF THE INVENTION

Figure 1:
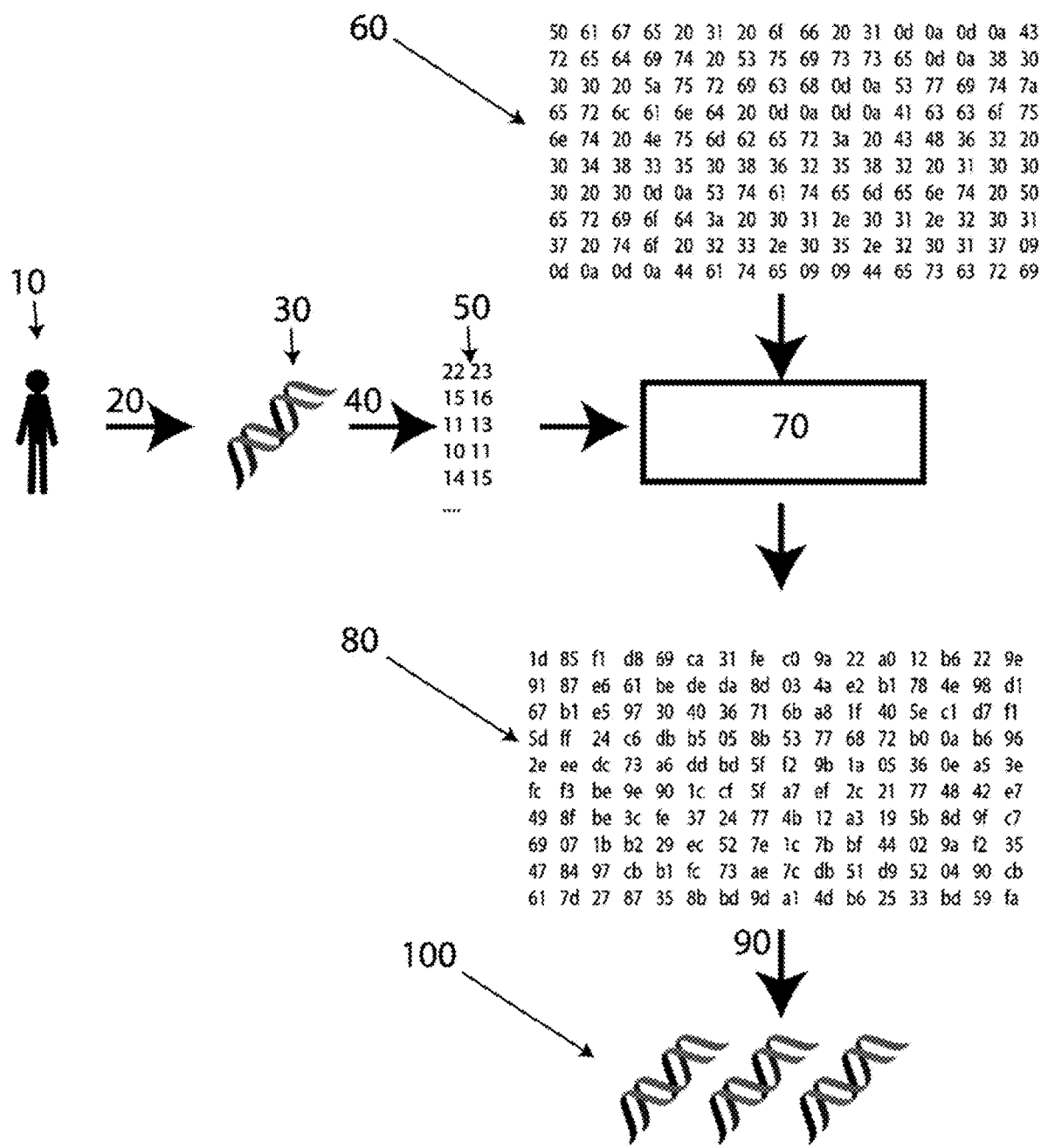
FIGS. 1-4 depict flowcharts illustrating high-level steps of methods of encoding or retrieving information, according to embodiments. In more detail.

Biometric technologies such as exemplified in the background section all have pros and cons. For example, small devices such as smartphone sensors mostly require partial matches of fingerprints, which can sometimes be tricked using a limited set of so-called "master fingerprints". Similarly, a face/iris scanner may not be able to distinguish an actual face/iris from a high-quality photo. Thus, the extent in which such biometrics authentication schemes make it possible to uniquely identify and discriminate identities of individuals is questionable. All the more, such techniques poorly fit into a context where information has to be encoded in or decoded from a sample containing synthetic DNA, which requires specific-purpose hardware (devices, apparatuses) for sequencing and/or synthetizing DNA.

Having realized this, the present Inventors have conceived and refined methods, and built devices, which essentially rely on the same kind of technology to encode/decode encrypted data and interpret cryptographic keys, to secure access to the information. I.e., using such methods, only predefined individuals (or persons possessing predefined entities) can effectively recover such information.

For example, on the encoding side: information is encoded in an encrypted form, using a key obtained based on, e.g., polymorphic features of nucleic acids from the requesting person. Next, upon decoding, polymorphic features of nucleic acids can be read (sequenced) together with digital information encoded in synthetic DNA, and the polymorphic features read are translated into a cryptographic key used to decipher the encoded information. As we shall see, the present approach is compatible with both symmetric and asymmetric encryption schemes.

Aspects of the invention are now described, which concerns methods to encode and retrieve information. Such methods may notably involve the following steps.

First, a personal key is generated by reading predefined polymorphic features of nucleic acids (RNA, DNA, mitochondrial DNA, genomic DNA, SiRNA) of a given person (a key individual). Such polymorphic features may for instance be single nucleotide polymorphisms (SNPs), variable tandem repeats (VTRs), short tandem repeats (STRs), microsatellites or any other polymorphic feature of nucleic acids. Depending on which polymorphic features are utilized, the key generated may not only be unique to a given person, but also to very close relatives of that given person.

For example, SNPs and STRs on the Y-chromosome are only inherited from father to sons, SNPs on the mitochondrial DNA are only inherited from mothers to children. Using other polymorphic features than those listed just above, and even if, e.g., the old 13 CODIS (Combined DNA Index System) STR loci are utilized, no two persons will generate the same key. I.e., the probability for two persons to have the same 13 CODIS STR profile is known to fall below $2 \cdot 10^{-14}$. As analysed (e.g., measured/sequenced by massively parallel sequencing or next-generation-sequencing, NGS), the polymorphic features can be translated into a key, e.g., a binary key, via any suitable algorithm (as exemplified below). The resulting should preferably have an entropy of at least 64 bits, and more preferably of at least 128 bits. For STRs, many loci are known and the best understood loci are described and used in the ESS (European Standard Set) database (loci: D3S1358, vWA, D8S1179, D21S11, D18S51, TH01, FGA, D1S1656, D2S441, D10S1248, D12S391, D22S1045) and the CODIS database (loci: CSF1PO, D3S1389, D5S818, D7S820, D8S1179, D13S317, D16S539, D18S51, D21S11, FGA, TH01, TPDX, vWA, D1S1656, D2S441, D2S1338, D10S1248, D12S391, D19S433, D22S1045). A collection of SNPs can be found in the public Single Nucleotide Polymorphism database (dbSNP) collected and published by the National Center for Biotechnology Information (NCBI). The number of polymorphic features utilized and the recorded variability of polymorphic features in the public can be used to calculate the expected variability and key strength (entropy). As an example, data encrypted according to an Advanced Encryption Standard (AES) algorithm, using a key entropy of at least 128 bits, cannot be deciphered in practice as even the fastest computer (100 petaflops) would require $\sim 10^{17}$ years to decipher the encrypted data in a brute force attack. As one may realize, such an entropy (variability) can indeed be obtained from, e.g., polymorphic features of STRs such as listed in the ESS and CODIS database.

Second, the generated key (e.g., unique to a person or a group of persons) is utilized to encrypt digital information. There, several encryption methods are known in the field of computerized cryptography, which could advantageously be used in the present context. During encryption, a message (e.g., plaintext) is encrypted into ciphertext, using a key and an encryption method. Even if someone can access the ciphertext, the latter can only be interpreted (i.e., deciphered) if decrypted using the correct key. Without having access to the right key, the message cannot be duly decrypted. For example, a symmetric encryption scheme may be used, such as an AES encryption scheme approved by the NIST (National Institute for Standards and Testing). The encrypted digital information is then translated into DNA sequences, for data encoding purposes. Here, several approaches can be contemplated, which may notably include an error correcting code. Suitable classes of error correction coding algorithms include, e.g., Reed Solomon codes, Fountain codes, Low-Density-Parity-Check-Codes, and Turbo-Codes.

The DNA sequences are subsequently synthesized as synthetic DNA. The DNA materials eventually obtained can then be stored and distributed as needed.

In variants to symmetric encryption schemes, asymmetric encryption can be relied upon. In this case, information is encrypted with a public key paired to a private key, which is itself generated from polymorphic features of nucleic acids, as described above, e.g., nucleic acids of a key individual (or a group of key individuals). In variants, any lifeform could also serve as a basis for encryption purposes, as noted earlier. Examples of suitable asymmetric encryption methods include algorithms derived from the so-called Rivest-Shamir-Adleman (RSA) method, the Digital Signature Standard (DSS), and Elliptic Curve Digital Signature (ECDSA). As noted in the summary, the private key may first be generated, in order to generate a corresponding public key. Next, the private key can nevertheless be safely deleted, inasmuch as it can be later re-generated, to decrypt the information. This may require for the requester to be able to keep track of the public key generated, especially if numerous keys have to be generated. In such cases, a suitable pairing system (whereby public keys indirectly point at corresponding private keys) may need be maintained by the requester, to be able to re-generate a private key corresponding to the public key used for encryption.

Third, for information retrieval from the synthetic DNA, synthetic sequences corresponding to the decryption key are preferably mixed with the synthetic DNA (and/or transcribed RNA). The DNA sequences may undergo pre-sequencing steps (Polymerase Chain Reaction, or length selection, ligation, etc.) In such embodiments, the two different DNA sources can advantageously be read together in one "sequencing run". I.e., the same device (DNA sequencing machine) as used to read the primary data simultaneously reads the encrypted data and the polymorphic features, based on any suitable sequencing method. Such polymorphic features are used to generate the key (e.g., the same as the encryption key or a private key) required to decipher the encrypted data. Again, all such operations can advantageously be performed using a single device. The device then identifies and utilizes the personal key as recovered to decipher the digital information and makes it accessible to the requesting entity (e.g., the key individual or group of key individuals).

In case the synthetic DNA sequences are read (sequenced) by someone not in possession of the right key or DNA material, the data read cannot be meaningfully decrypted; such data remains useless as it cannot be interpreted for any relevant purpose. Note, the underlying system may be configured to take either (i) a binary key as input or (ii) a decryption sample, from which the decryption key is generated. Preferably though, the system may only accept a decryption sample as input, such that a malicious person who would have had access to the binary key could not cause to decrypt the original information.

The technology of DNA sequencing is rapidly advancing. DNA sequencing devices costing less than 1 000 USD are available and it was recently shown that such devices can be utilized to identify persons based on genomic polymorphisms. Such DNA sequencing devices can be used as part of a biometric access system, e.g., in a laptop or a cell phone. Now, and as it may be realized, such devices can advantageously be modified so that they can detect the sequencing data corresponding to the key and compute the key from the sequencing data. Such devices may accordingly be configured to detect the sequencing data corresponding to the encrypted information and utilize the key to decrypt the information. Note, the resulting devices do not need to transmit (output) the polymorphic features of the genomic sample or the sequence data of the information. Rather, such devices only transmit (output) the decrypted information (or attempted decrypted information if the incorrect polymorphic features are presented).

Next, several techniques and devices suited for storing synthetic DNA samples (encoding digital information) are available (e.g., DNA in solution, dry DNA, encapsulated DNA), which all rely on DNA material. The terminology 'DNA Vault' as used herein is understood as including any physical item (consumer good, hard drive, well plate, tube, safe, etc.) containing synthetic DNA material storing encrypted information, encoded as described herein. Now, if a decryption key is derived from inherited polymorphic features (e.g., from mitochondrial DNA, or Y-chromosome), then the same key can be generated from any person of a group of persons with a common ancestry. A DNA vault comprising such DNA samples encoding encrypted information as described herein is termed a 'DNA family vault' in this description.

A DNA vault and a DNA family vault as defined above include synthetic DNA material obtained thanks to the present encoding methods. Such vaults may further be used as part of another object, device or system, e.g., as part of restricted-access device, object, apparatus or facility, or in any other useful system where information storage is in the interest of an individual or a group of individuals.

Synthetic DNA samples obtained thanks to the present methods are characterized by the fact that they carry encrypted information. Information encoded therein translates into specific features of the synthetic DNA material, and the key to decipher such information can be computed from the polymorphic characteristics of the nucleic acids of a suitably chosen entity (or entities), such as an individual (or a group of individuals). The DNA sample can then be stored in a vault or a family vault. If it is attempted to access information stored on a DNA sample of this vault without an appropriate decryption key, the information recovered, if any, will remain encrypted and will thus not be interpretable. On the other hand, attempting to access the original information in combination with data extracted from the polymorphic characteristics of rightful nucleic acids results in that the information can be deciphered and interpreted. This allows the present DNA samples to be distinguished from ordinary DNA samples (natural DNA, or synthetic DNA material encoding non-encrypted data, etc.). That is, ordinary DNA material can be DNA of biological origin or synthetic DNA created for different purposes. Ordinary DNA is traditionally characterized through its chemical or biological function, typically together with a sequence information.

Characterizing DNA materials with traditional characterization methods will not permit such a distinction. On the contrary, a suitable test must involve polymorphic characteristics of nucleic acids of the subject entities, to derive a key. This involves the identification or knowledge of the subject entities, as well as the type of algorithms used throughout the decoding steps. Once the subject entities (e.g., key individual or group of key individuals) and the employed methods are known, a simple, two-step test can be used to distinguish the present DNA samples from ordinary DNA, which is described below.

This two-step test relies on the following, preliminary assumptions:
A subject entity or entities (e.g., key individual or group of key individuals) is identified;
A method for digital information encoding/decoding (i.e., translation from digital to DNA sequence and back) is chosen;
An encryption/decryption method is chosen;
Polymorphic features utilized for the key and a method to calculate the decryption key from the polymorphic features is chosen. This calculation may use helper data stored separately.
A nucleic acid sequencing method is chosen.
An expected level of information interpretability (i.e., data purpose, e.g., file format, information content) is chosen, meaning that, once decrypted, this information is useful to (i.e., interpretable by) a machine or a person without inconsiderable computational effort (e.g., a brute force attack). Such information can be used to differentiate useful binary data (following successful decryption) from non-useful binary data (following unsuccessful decryption) in the test procedure.

Test Procedure:
Biological nucleic acids are derived from a suitable entity, e.g., an individual (or a group of individuals), and chosen polymorphic features thereof are measured by the chosen nucleic acid sequencing method;
A decryption key is generated from the polymorphic features using the chosen calculation method;
The DNA sample is sequenced using the chosen sequencing method;
The sequence is decoded using the chosen decoding method, thereby yielding encrypted information; and
The decryption method is performed using the encrypted information as cyphertext and the decryption key, leading to decrypted information.

Two-Step Test:
1. The procedure is executed with the synthetic DNA sample and the biological nucleic acids are derived from the rightful entity; and
2. The procedure is executed with the synthetic DNA sample; the biological nucleic acids are not derived from the rightful entity, but from another entity.

Test Results:
If the synthetic DNA sample is a synthetic DNA sample according to embodiments of the present invention, then:
Information processed as in step 1 above is useful for the chosen purpose, whereas
Information processed as in step 2 above is not useful for the chosen purpose.
No synthetic DNA sample, other than DNA samples according to embodiments results the same set of results for the above two-step test.
Any ordinary DNA sample will result in a different test result, and will either:
Not be useful for the chosen purpose for both steps of the tests, or
Be useful for the chosen purpose for both steps of the test, or
Not be useful for the chosen purpose in step 1 above of the test and be useful for the chosen purpose in step 2 of the test.

If, additionally, the decryption step (i.e., the key generation from sequence data and mathematical decryption) is implemented as an integral part of the sequencing device (i.e., implemented in hardware), data recovery is only possible if, e.g., synthetic DNA and genomic DNA from the chosen subject entity are simultaneously available in a sequencing pool. For practical purposes, DNA samples according to embodiments will preferably be stored together with the sequencing device. As one understands, such DNA materials are particularly useful for the creation of a vault or a family vault.

In a stronger mode of operation, the synthetic DNA is generated in a way that it chemically interacts (by base-pairing) with genomic DNA of the subject entity, such that the decryption code can only be generated after this chemical interaction has occurred. Now, this interaction may not be predictable for the corresponding DNA sequences. Suitable chemical interactions and base pairing molecules are known in the art.

In variants, the key is not only generated from genomic DNA from the subject entity, but also generated from polymorphic features of specific RNA sequences (e.g., SNPs), it being reminded that RNA rapidly degrades and is very difficult to store. Therefore, the biometric sample (e.g., buccal swab) would have to be fresh, which further makes it possible to simply distinguish a live subject from a dead subject (contrary to, e.g., traditional fingerprint scanning and iris scans). In such variants, access to information may somehow be linked to the physical presence of the subject entity (e.g., a key individual or group of key individuals) close to the device used for information retrieval. Such limited access to information is particularly useful for personal information of high value to the requester.

Aside from the authentication of key individuals for access to data, the method described above, also allows access to privileged groups (group of privileged individuals), if the group members are close relatives (e.g., family) or otherwise genetically related. If, e.g., nucleic acid polymorphisms of the Y-chromosome are used for generating the key, the decrypted data would only be readable by a father and his sons. If genetic markers of mitochondrial DNA would be introduced, the data would be readable by a mother and her descendants. In such variants, information can be safely transferred from one generation to another.

In other embodiments, the encryption/decryption keys may be generated from the polymorphic features of the nucleic acids of two or more individuals (group of multiple individuals), whereas the key contains elements of each individual. In such cases, decrypting information as initially encrypted by such a key requires measuring the polymorphic features of the same individuals for decryption and information recovery. That is, access to the original information is only possible if genomic nucleic acid samples of the corresponding group are available, and, ideally, if the corresponding group of individuals is physically present for the generation of fresh nucleic acid samples, and possibly close to the system used for information retrieval.

More advanced embodiments further rely on helper data. Namely, a general data decryption key may possibly be derived from helper data (in addition to polymorphic features of nucleic acids of an individual), see FIG. 3, in order to allow several individuals (a variable group of individuals), and/or new individuals, which would require new key individual enrolment) to decipher the encrypted data. For example, during the enrolment of a new individual, predefined polymorphic features of the nucleic acids of this individual are measured/sequenced and utilized to compute a personal key using a key computation function. This key is then hashed by a cryptographic hash function to generate a cryptographic hash of the personal key. This hash is then mapped with a general data decryption key with a predefined mapping function to generate a helper dataset. As neither the personal key of the new individual, nor the general data decryption key can be derived based on the sole knowledge of the helper data (i.e., without access to either the personal key or the general decryption key), this specific helper dataset can be translated into a DNA sequence and synthesized to form a synthetic DNA material. This material contains the helper key, which can be stored together with the DNA material containing the encrypted digital information.

In variants, the helper data can be made public. During data recovery, the predefined polymorphic features of a key individual are measured/sequenced together with the encrypted information and the helper data stored in the synthetic DNA material. The measured polymorphic features of the individual are then utilized to compute the personal key, thanks to the key computation function. This key is then hashed by the cryptographic hash function to generate the cryptographic hash of the personal key. Having access to both the helper data and the cryptographic hash of the personal key, the general data decryption key can be computed by inverting the mapping function (assuming the latter is invertible). This general data decryption key is then utilized to decrypt the information stored in the synthetic DNA. Accordingly, such variants still make it possible to change access rights over time. I.e., selected key individuals can still decrypt the original information as stored on the synthetic DNA sample, while a group of (allowed) key individuals can be changed by adding/removing new helper datasets. Note, a "group of individuals" as used herein may include a group of privileged individuals, a group of multiple individuals, or a group of variable individuals as described above, where the number of people in a group of key individuals is larger than or equal to one. In addition, and as noted earlier, the notion of "key individuals" extends to "key entities", these including any entity from which suitable nucleic acids can be analysed, for the purpose of generating a cryptographic key.

Compared to already known biometric methods (e.g., relying on fingerprints, iris-scans, face-scans), the advantage of using genomic DNA features to generate a biometric key for data encryption/decryption, is fourfold:

Personal genomic DNA features can normally be measured with higher precision;

Massive knowledge on the variability of personal genomic DNA features (e.g., in the population) is already available, e.g., from forensics, which improves credibility of the method;

Personal genomic DNA features including STRs and SNPs enable high entropy keys; and The encrypted digital data and decryption key can be measured simultaneously within the same device (sequencer), as they are both present in the form of nucleic acids.

The accompanying drawings further illustrates embodiments of the invention.

In detail, FIG. 1 is directed to a specific method of encoding encrypted information in a synthetic DNA material. Assume a person 10 provides a buccal swab. Genomic DNA 30 is extracted 20 and individual personal markers are read using a suitable sequencing technology 40 to yield a list of individual markers 50. This list of individual markers is converted to a key, and this key is used in an encryption protocol 70 to encrypt digital information 60 yielding the desired encrypted, digital information 80. The encrypted information is then translated into DNA sequences and synthesized 90 to yield a DNA pool 100 carrying the encrypted information.

Figure 2:
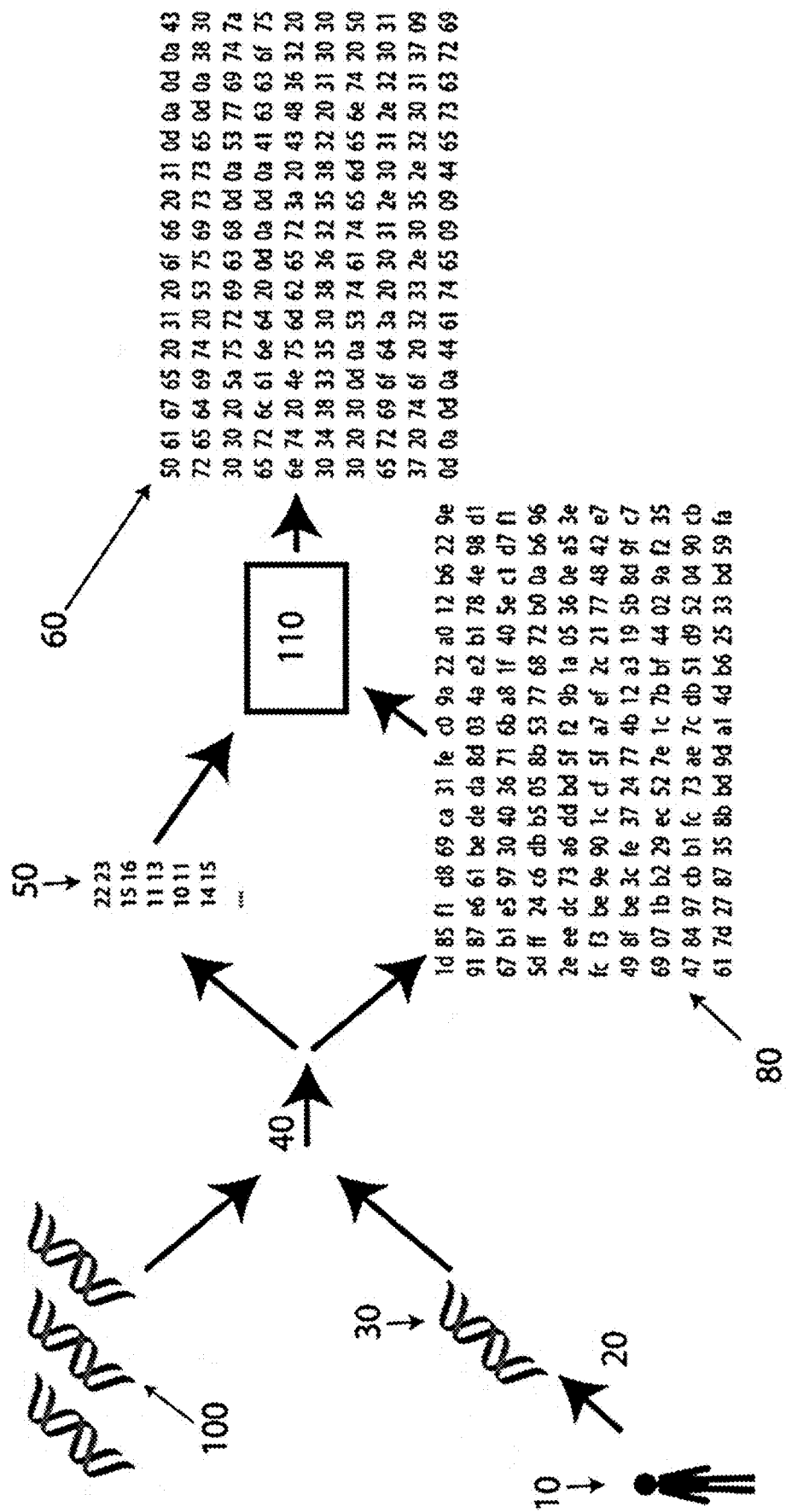

FIG. 2 illustrates a method of retrieving information encoded thanks to a method as in FIG. 1. The DNA data pool 100 is mixed with genomic DNA 30, which has been extracted 20 from an individual 10. The mixture is sequenced in one sequencing run 40, and the sequencing data is utilized to read both the personal markers of the individual as well as the decrypted digital information 80. A decryption protocol 110 uses the list of personal markers 50 to calculate a key to decipher the digital information, thereby yielding the original information 60.

Figure 3:
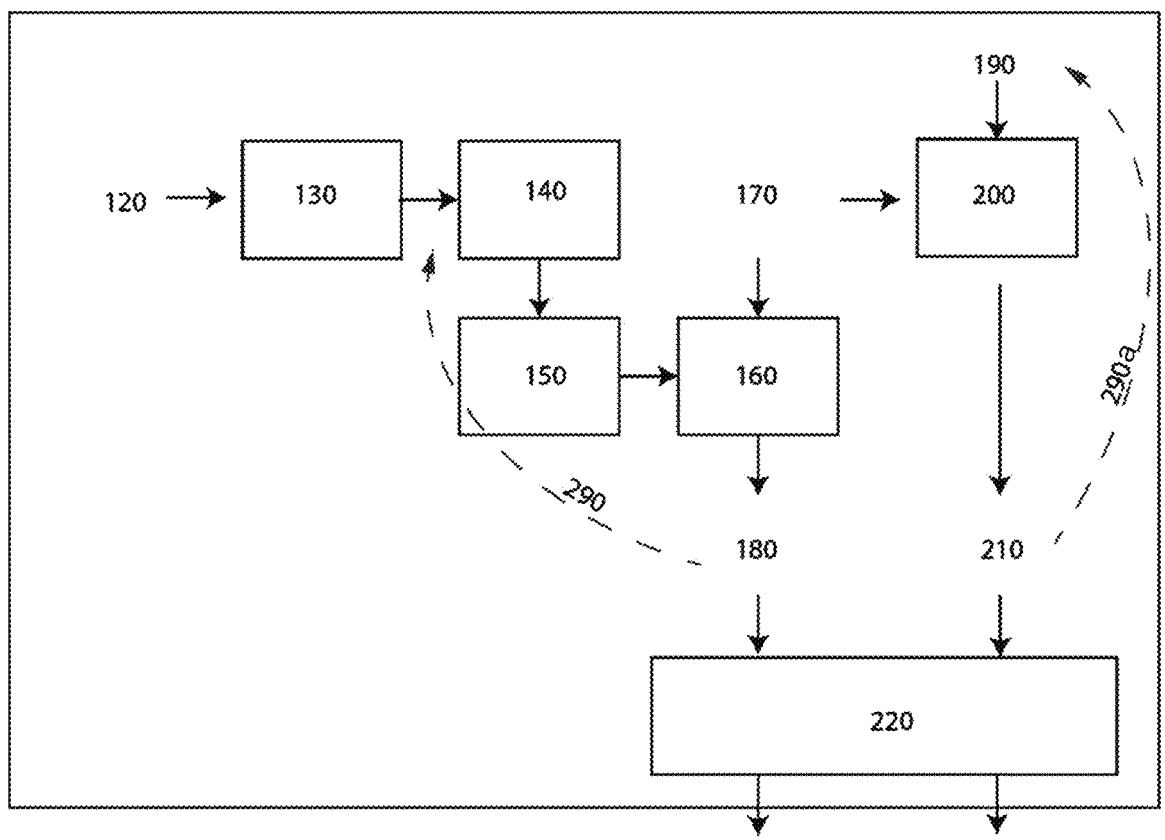
Figure 3:
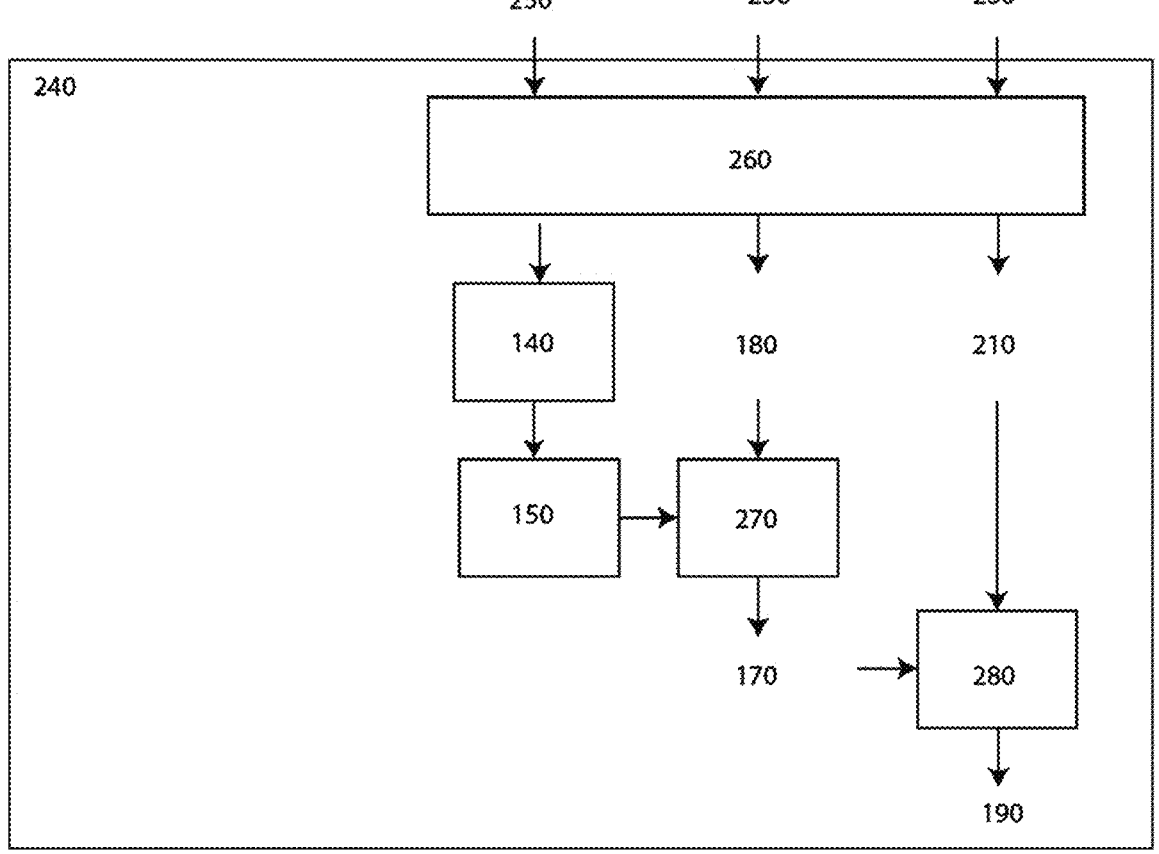

FIG. 3 shows the mode of operation allowing the addition of a new key individual by the utilization of helper data. During enrolment, the nucleic acids of the new key individual 120 are analysed/sequenced 130 to generate the polymorphic properties of the nucleic acids and a personal key 140 is derived for this individual. This personal key is hashed with a cryptographic hash function to generate a hash 150 of the personal key. This hash is mapped 160 with the general decryption key 170 to generate helper data 180. Sensitive data 190 is encrypted using an encryption method 200 to generate encrypted data 210. The helper data 180 and the encrypted data are translated to DNA and synthesized 220 to yield DNA materials 230 for storage.

For data recovery 240, the nucleic acids of a key individual 250 are sequenced 260 together with the DNA in the DNA materials 230 to yield helper data 180, polymorphic properties of the nucleic acids resulting in a personal key 140 and encrypted data 210. The personal key is hashed to generate the hash 150 of the personal key. Using the inverse of the mapping function 270 with the personal key hash 150 and helper data 180 as input, the general decryption key 170 is computed. In the decryption stage 280, the general decryption key is utilized to decrypt the information, thereby resulting in decrypted data 190. The decrypted information and helper data can be made public as it is computationally hard (if not infeasible) to: (i) generate the personal key from the sole helper data 180 (see the path denoted by arrow 290), owing to the hashing operation 150 performed with the hash function; and (ii) compute the sensitive data from the sole encrypted information due to the encryption function 200 (see the path indicated by arrow 290a).

Figure 4:
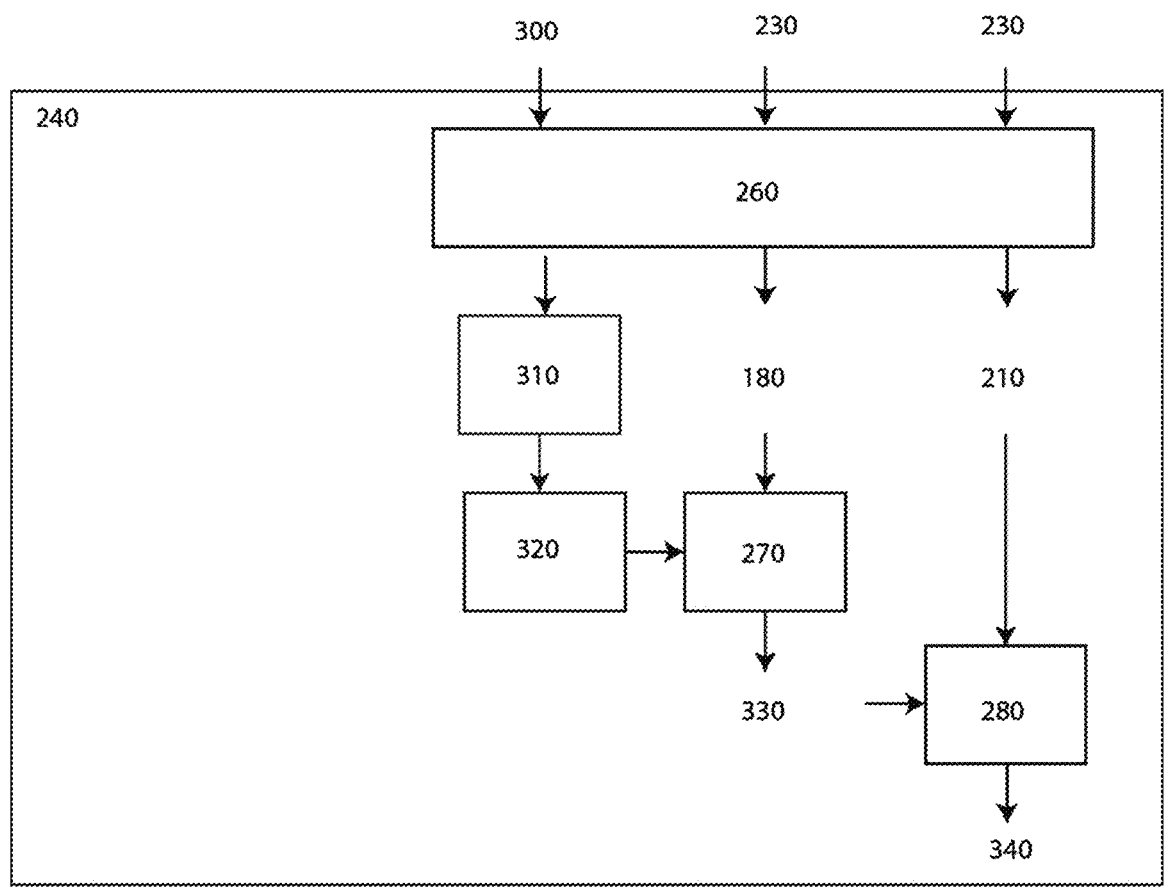

FIG. 4 illustrates an attempted data recovery process 240 using, on the one hand the same DNA material 230 as in FIG. 3, and, on the other hand, non-authorized nucleic acids 300, i.e., material from an individual that is not in the allowed group of key individuals. In this case, the sequencing step yields helper data 180, the encrypted data 210 and the personal key 310 of the non-authorized individual. Using the inverse of the mapping function 270 with the hash obtained from this personal key 320 together with helper data 180 as input, a key 330 is computed that differs from the general decryption key. Using the resulting key 330 in the decryption stage 280 cannot possibly lead to the information requested, but rather yields information 340 that cannot be interpreted.

The following, non-limitative examples are intended to further illustrate embodiments of the invention.

Example 1: Key Generation, Data Encryption and DNA Synthesis

The genomic DNA of a person (Person A=key individual) is obtained from a buccal swab and then purified. The DNA is mixed with a PCR primer mix of STR loci, e.g., the loci D2S1338, D3S1358, D5S8181, D7S820, D8S1179, D13S317, D16S539, D18S51, D19S433, D21S11, CSF1PO, FGA, PentaD, PentaE, TH01, TPDX, and vWA. Next, PCR is performed, and appropriate sequencing adaptors are introduced by ligation. The generated amplicons are sequenced on a suitable sequencing machine. From the sequence information, the individual alleles are read, identified and indexed. For Person A this results in the alleles 22, 23; 15, 16; 11, 13; 10, 11; 14, 15; 10, 12; 9, 9; 16, 18; 13, 15; 29, 30; 11, 11; 19, 20; 12, 12; 7, 16; 7, 7; 8, 11; 14, 15 in this example. This information is used together with a translator subtracting minimal known alleles for each locus and converting resulting number to binary, so as to generate the following 128 bits Person-A key:
01110110100010100101100011011001010101000-100000001101001000100010000111000011
000010000001100110010001001011010001011110100-110001

Confidential information (e.g., a bank statement, say 288 bytes long) is encrypted with the generated Person-A bits key, using AES encryption (ECB mode). The digital data obtained is then translated to DNA with, e.g., any publicly available or proprietary translation method, generating ~17 sequences of 158 nucleotides length (including primer regions) and including approximately 20% redundancy as generated by Reed-Solomon encoding. Such sequences are then synthesized to DNA, e.g., using an automated synthesis tool or a service provider (offering DNA synthesis as a service). There, the DNA may for example be amplified by PCR, dried, and stored in a dry environment until read-out. Note, should an external service provider be used for that purpose, this provider solely has access to encrypted information, which per se is useless, as the service provider cannot decipher the information in practice. The same holds for any receiver of the encrypted digital information, or the synthetic DNA, who does not have access to the private key, or the natural DNA (and/or RNA) of the key individual.

Example 2: Information Retrieval from Synthetic DNA by the Key Individual

For information retrieval of the synthetic DNA, the information requestor (Person A=key individual) provides a buccal swab sample. The DNA is extracted from the swab, mixed with PCR primer of the STR loci as given in example 1. The resulting amplified DNA is mixed with the synthetic DNA (which may also have been prepared for sequencing by introduction of appropriate adaptors) in a 1:1 ratio (by mass of DNA). This sequencing library now simultaneously contains the encrypted information as well the decryption key of Person A—both in the form of DNA. Upon sequencing this library using any suitable sequencing techniques and appropriate data handling (analysis of alleles, generation of binary key; translating of synthetic DNA sequence back to binary with subsequent decoding) the encrypted digital data and the decryption key of person A are simultaneously accessible as digital information. In detail, the resulting data is analysed in order to search for the key generation sequences (the sequences starting with one of the STR primer regions). From these DNA sequences, the alleles are read, identified and indexed. For person A this results, in this example, in alleles 22, 23; 15, 16; 11, 13; 10, 11; 14, 15; 10, 12; 9, 9; 16, 18; 13, 15; 29, 30; 11, 11; 19, 20; 12, 12; 7, 16; 7, 7; 8, 11; 14, 15. Such information is together with a suitable translator to generate the following, personal key (for person A):
01110110100010100101100011011001010101000010-00000011101100100010001000011100011
000010000001100110010001001011010001011110100-110001.

The remainder of the sequences (synthetic sequences) are then translated back into encrypted digital data, using a method known per se, and the 128 bit-long key is utilized to decrypt the resulting information using the AES-128 method to make the information interpretable. The deciphered text will be identical (in the framework of, e.g., ASCII coding) to the original text.

Example 3: Information Retrieval from Synthetic DNA by an Individual Who is not an Authorized Individual (not a Key Individual)

For an attempt of information retrieval from synthetic DNA, the information requestor (Person B=not the key individual) provides a buccal swab sample. The DNA is extracted, mixed with PCR primer of the STR loci as in example 1. The amplified DNA is mixed with the synthetic DNA (prepared as before, by introduction of appropriate adaptors) in a 1:1 ratio by mass of DNA. This sequencing library now simultaneously contains the encrypted information as well the decryption key of Person B—both in the form of DNA. Upon sequencing this library and appropriate data handling (analysis of alleles, generation of binary key; translating of synthetic DNA sequence back to binary with subsequent decoding) the encrypted digital data and Person B decryption key are simultaneously accessible as digital information. From these DNA sequences, alleles are read, identified and indexed, which results (for Person B) this results in the alleles 17, 20; 14, 15; 12, 12; 9, 10; 15, 15; 12, 12; 11, 12; 12, 18; 14, 15; 29, 31; 11, 12; 21, 24; 7, 13; 17, 18; 6, 8; 8, 9; 17, 17. This translates into the following binary sequence:

00100011011001101100011010011101011001000110-
00110011011001010100010001001001001
00010000010101001010011000110100101001101 1011-
00011.

Obviously, this key differs from the key previously derived for person A. The remainder of the sequences (synthetic sequences) are then translated back to encrypted digital information. Using the decryption key derived from Person-B to decipher this information (based on the AES-128 method) results in ASCII such as "²g.δa.œîˆ=.&s ¢ì<<.0osì.àâ~.ñˋ òi.;", which cannot be interpreted and is therefore useless.

While the present invention has been described with reference to a limited number of embodiments, variants and the accompanying drawings, it will be understood by those skilled in the art that various changes may be made and equivalents may be substituted without departing from the scope of the present invention. In particular, a feature recited in respect of a given embodiment of an encryption method can be contemplated for use in a corresponding decryption embodiment, without departing from the scope of the present invention. Also, features shown in a drawing may possibly be included or combined with features explicitly evoked in the description, still without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated.

What is claimed is:

1. A method for encoding information, wherein the method comprises:
   generating an encryption key according to polymorphic features of nucleic acids from one or more entities;
   encrypting information based on the generated key; and
   encoding the encrypted information into synthetic DNA, the encoding comprising:
      translating digital information capturing the encrypted information into a sequence combining natural nucleotides of DNA, and
      synthesizing the sequence into a synthetic material of physical DNA to form said synthetic DNA.

2. The method according to claim 1, wherein
the encryption key is generated from the polymorphic features of DNA or RNA of the one or more entities.

3. The method according to claim 2, wherein
the encryption key is generated from one of:
short tandem repeats of the DNA of the one or more entities;
short tandem repeats of the DNA of the one or more entities as alleles identified by sequencing five or more of predefined, genomic Loci of the one or more entities;
a set of single nucleotide polymorphisms of the DNA or RNA of the one or more entities;
mitochondrial DNA of the one or more entities; and
a Y-chromosome of the one or more entities.

4. The method according to claim 3, wherein
the encryption key is generated from a set of single nucleotide polymorphisms of DNA or RNA of the one or more entities, and said set comprises at least five single nucleotide polymorphisms, and generating the encryption key further comprises identifying said at least five single nucleotide polymorphisms by sequencing the nucleic acids of said one or more entities.

5. The method according to claim 1, wherein
the method further comprises generating one or more helper datasets from the encryption key generated and said polymorphic features, and
encoding the encrypted information further comprises storing the one or more helper datasets generated on said synthetic DNA, along with said encrypted information.

6. The method according to claim 1, wherein
said information is encrypted based on a symmetric encryption algorithm, such that said encrypted information can be decrypted using a key identical to said encryption key.

7. The method according to claim 6, wherein
the method further comprises, after having encrypted said information, deleting both the encryption key and material from which said encryption key was generated, without transmitting any of the encryption key and said material.

8. The method according to claim 1, wherein generating the encryption key further includes:
measuring said polymorphic features of said nucleic acids; and
translating the measured polymorphic features into a cryptographic key.

9. The method according to claim 1, wherein
the method further comprises, prior to generating said encryption key, generating a private key based on said polymorphic features of said nucleic acids of a given sample from said one or more entities, whereby said encryption key is generated based on the generated private key and paired to the generated private key, and
said information is encrypted based on an asymmetric encryption algorithm using the generated encryption key as a public key, such that said encrypted information can only be decrypted using a private key identical to the generated private key.

10. The method according to claim 9, wherein the method further comprises, after having encrypted said information:
deleting both the private key generated and material from which said private key was generated, without transmitting any of the private key and said material; and
re-generating a private key based on polymorphic features of nucleic acids of another sample from said one or more entities, so as to be able to decrypt said encrypted information.

11. A method of retrieving information, the method comprising
providing synthetic DNA encoding encrypted information, wherein the synthetic DNA is a synthetic material of physical DNA that has been obtained by:
   translating digital information capturing the encrypted information into a sequence combining natural nucleotides of DNA, and
   synthesizing the sequence into the synthetic material of physical DNA to form said synthetic DNA; and
reading the encrypted information by sequencing the synthetic DNA provided and decrypting the information read using a decryption key generated according to polymorphic features of nucleic acids from one or more entities.

12. The method according to claim 11, wherein reading the encrypted information further comprises:

sequencing said polymorphic features, so as to generate said decryption key, in order to decrypt the information read.

13. The method according to claim 11, wherein reading the encrypted information further comprises mixing sequences of the synthetic DNA provided with genomic sequences containing said polymorphic features whereby sequences of said polymorphic features and sequences of said synthetic DNA are simultaneously sequenced.

14. The method according to claim 13, wherein the method further comprises, after mixing said sequences:
processing a mixture obtained by mixing the sequences of the synthetic DNA with sequences of said nucleic acids to generate a sequencing pool; and
sequencing the sequencing pool generated using a massively parallel DNA sequencing method.

15. The method according to claim 11 wherein the synthetic DNA provided is sequenced based on a massively parallel DNA sequencing method.

16. The method according to claim 11, wherein the method further comprises generating the decryption key based on helper data, in addition to said polymorphic features, whereby said polymorphic features are combined with said helper data to compute the decryption key.

17. The method according to claim 16, wherein the method further comprises reading one or more helper datasets stored on said synthetic DNA, along with said encrypted information, to obtain said helper data.

18. A DNA vault, wherein
the DNA vault comprises one or more containers, each storing one or more samples of synthetic DNA encoding information, wherein
information is stored on each of the one or more samples in an encrypted form, which has been obtained according to an encryption key generated according to polymorphic features of nucleic acids from one or more entities, and
the synthetic DNA is a synthetic material of physical DNA and said information has been encoded into the synthetic DNA by:
translating digital information capturing the encrypted information into a sequence combining natural nucleotides of DNA, and
synthesizing the sequence into the synthetic material of physical DNA to form said synthetic DNA.

19. The DNA vault according to claim 18, wherein one or more helper datasets are further stored on each of the one or more samples of synthetic DNA, along with said encrypted information.

20. The DNA vault according to claim 18, wherein:
the DNA vault is a family vault, whereby at least one of the DNA samples stored encodes information encrypted with a respective encryption key generated according to inherited polymorphic features of nucleic acids from said one or more entities.

\* \* \* \* \*